(12) United States Patent
Dong et al.

(10) Patent No.: US 8,743,365 B2
(45) Date of Patent: Jun. 3, 2014

(54) APPARATUS AND METHOD FOR ON-LINE, REAL-TIME ANALYSIS OF CHEMICAL GASES DISSOLVED IN TRANSFORMER OIL

(75) Inventors: Bo Dong, Blacksburg, VA (US); Anbo Wang, Blacksburg, VA (US); Jianmin Gong, Blacksburg, VA (US)

(73) Assignee: Virginia Polytechnic Institute & State University, Blacksburg, VA (US)

( * ) Notice: Subject to any disclaimer, the term of this patent is extended or adjusted under 35 U.S.C. 154(b) by 52 days.

(21) Appl. No.: 13/473,227

(22) Filed: May 16, 2012

(65) Prior Publication Data

US 2012/0300210 A1 Nov. 29, 2012

Related U.S. Application Data

(60) Provisional application No. 61/487,767, filed on May 19, 2011.

(51) Int. Cl.
*G01N 21/00* (2006.01)

(52) U.S. Cl.
USPC .......................................... 356/437; 356/432

(58) Field of Classification Search
USPC ......... 356/432–444, 326, 328, 246, 410, 319; 250/573, 373, 343, 339.13
See application file for complete search history.

(56) References Cited

U.S. PATENT DOCUMENTS 5,680,209 A * 10/1997 Machler .................. 356/319

\* cited by examiner

*Primary Examiner* — Tri T Ton
(74) *Attorney, Agent, or Firm* — Trego, Hines & Ladenheim, PLLC

(57) ABSTRACT

An inspection probe for directly measuring a transmission spectrum of a solvent oil in a transformer includes a tube having a plurality of apertures spaced along a side of the tube to allow oil to pass therethrough, and first and second optical collimators disposed at opposing ends of the tube. The first and second collimators are aligned by the tube such that incident light is transmitted through the first collimator, the tube, and the second collimator to a spectrometer.

7 Claims, 2 Drawing Sheets

APPARATUS AND METHOD FOR ON-LINE, REAL-TIME ANALYSIS OF CHEMICAL GASES DISSOLVED IN TRANSFORMER OIL

This application claims the benefit of Provisional Application No. 61/487,767 filed on May 19, 2011.

BACKGROUND OF THE INVENTION

This application relates to an apparatus and method for on-line, real-time dissolved gas analysis of transformer oil.

A high voltage transformer is one of the most important and expensive devices in the power industry. A single transformer failure can easily drive costs to more than 10 million dollars. Presently, high voltage transformers are monitored using on-line dissolved gas analysis (DAG) of transformer oil in conjunction with a transformer asset manager to diagnose faults occurred in transformers and prevent catastrophic failures.

Current dissolved gas analysis (DGA) methods extract dissolved gases out of the oil and measure the concentration of these gases in gaseous phase. While this method is in line with the IEEE guide on DGA for transformers, it is not convenient and cannot provide in-situ information.

BRIEF SUMMARY OF THE INVENTION

These and other shortcomings of the prior art are addressed by the present invention, which provides an apparatus and method which allows more accurate and localized dissolved gas information to be detected and used for transformer health condition monitoring and diagnostics.

According to one aspect of the present invention, an inspection probe for directly measuring a transmission spectrum of a solvent oil in a transformer includes a tube having a plurality of apertures spaced along a side of the tube to allow oil to pass therethrough, and first and second optical collimators disposed at opposing ends of the tube. The first and second collimators are aligned by the tube such that incident light is transmitted through the first collimator, the tube, and the second collimator to a spectrometer.

According to another aspect of the invention, a method of providing real-time analysis of chemical gases in a transformer oil includes the steps of providing an inspection probe adapted to measure a transmission spectrum of a solvent oil in a transformer, placing the probe inside a transformer, using the inspection probe to measure a transmission spectrum of the solvent oil, and determining the concentration of dissolved gases in the transmission oil.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
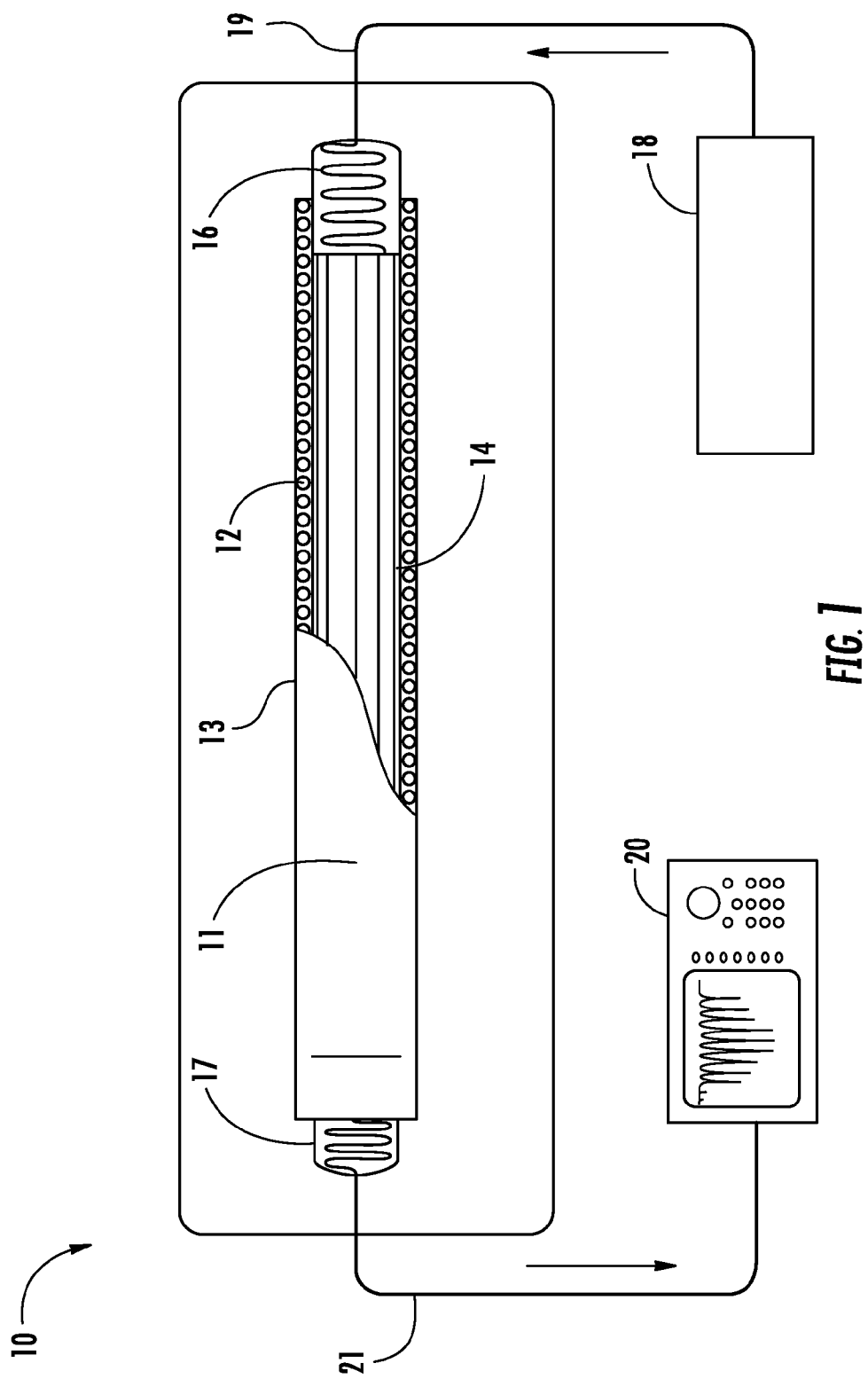
FIG. 1 shows an inspection probe for measuring a transmission spectrum.

Referring to the drawings, an exemplary inspection probe for directly measuring a transmission spectrum of a solvent oil in a transformer according to an embodiment of the invention is illustrated in FIG. 1 and shown generally at reference numeral 10.

The inspection probe 10 because of its compact size, immunity to electromagnetic interference, and high resistance to electric stress and multiplexing properbility can be installed inside high voltage transformers to give more accurate, prompt, and localized analysis of the state of a transformer.

As shown, the probe 10 includes a straight silica tube 11 with holes 12 and dust filters 13 on its sidewall 14 to allow oil to pass therethrough, and first and second optical collimators 16, 17 installed at opposing ends of the tube 11. The collimators 16 and 17 are aligned by the silica tube 11 such that incident light from a light source 18 can be transmitted through the first collimator 16 via a fiber optic cable 19, the silica tube 11, and the second collimator 17 to a spectrometer 20 with a low power loss via a fiber optic cable 21. The dust filter 13 is made of dielectric porous material which prevents invasion of large particles into the light channel. It should be appreciated that the dust filter 13 may be made of any suitable material for use with the probe 10 and to prevent invasion of large particles.

Because the probe 10 is immune to electromagnetic interference and can also resist large electric stresses inside high voltage transformers, it can be installed much closer to fault sources than current systems, which makes an analysis more accurate and prompt. Since the probe 10 is very compact and multi-plexible, multiple probes 10 may be installed at different locations in a transformer to get localized information which aids in diagnosing a fault source and its properties.

In use, the concentration of dissolved acetylene or other gases (such as hydrogen, ethylene, methane, ethane, and carbon monoxide) is obtained by directly measuring the transmission spectrum of the solvent oil. The measurement uses a gases unique absorption when dissolved in oil or other solvents. The advantage of this method is that more accurate and localized dissolved gas information can be detected, which is very useful for transformer health condition monitoring and diagnostics. The probe 10, which is intrinsically safe and immune to electromagnetic interference (EMI), may be placed inside the transformer for real-time in-situ DGA.

Figure 2:
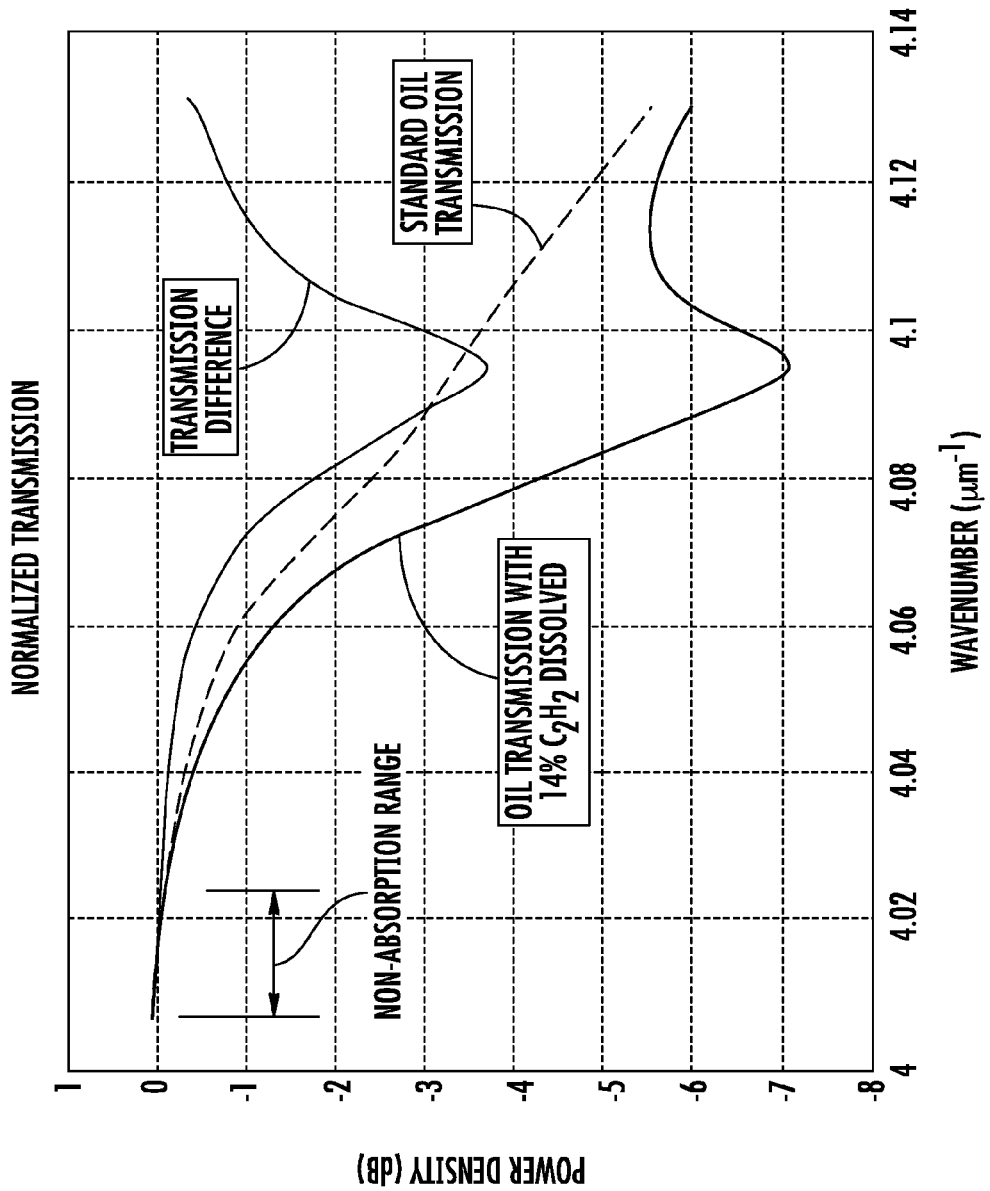
FIG. 2 shows normalized transmission spectra of transformer oil using the probe of FIG. 1.

Referring to FIG. 2, a normalized transmission spectra without and with acetylene dissolved inside transformer oil is shown. Dissolved acetylene produces an absorption dip around a wave number of about 4.095 $\mu m^{-1}$, the shape of the absorption dip is quite stable and the depth of the dip is proportional to the concentration of the dissolved acetylene according to both Beer-Lambert law and our test results. Outside the absorption dip region is a wide non-absorption region. The ratio of the light power at absorption region over that at non-absorption region is a function of the concentration of the dissolved acetylene and is not sensitive to the fluctuation of the source power and transmission loss, so the sensor can be regarded as self-calibrated.

Averaging may also be used to improve the signal-to-noise ratio of the detected spectra. And, since the shape of acetylene-absorption spectrum is quite stable, spectra correlation technique can be adopted to improve the decoding accuracy of the concentration of the dissolved acetylene.

It should be appreciated that the probe 10 structure is not limited to the current design and that any suitable optical device that can efficiently measure the transmission spectrum of transformer oil may be used.

The foregoing has described an apparatus and method for on-line, real-time analysis of chemical gases dissolved in transformer oil. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

We claim:

1. An inspection probe for directly measuring a transmission spectrum of a solvent oil in a transformer, comprising:
   (a) a tube having a plurality of apertures spaced along a side of the tube to allow oil to pass therethrough;
   (b) first and second optical collimators disposed at opposing ends of the tube; and
   (c) wherein the first and second collimators are aligned by the tube such that incident light is transmitted through the first collimator, the tube, and the second collimator to a spectrometer.

2. The inspection probe according to claim 1, further including dust filters positioned over the apertures to prevent debris from entering the tube.

3. The inspection probe according to claim 2, wherein the dust filters are formed of a dielectric porous material.

4. The inspection probe according to claim 1, wherein the incident light is transmitted by a fiber optic cable.

5. The inspection probe according to claim 1, wherein the tube is a silica tube.

6. The inspection probe according to claim 1, wherein the incident light is transmitted to the first collimater for transmission through the tube to the second collimator by a fiber optic cable connected to a light source.

7. The inspection probe according to claim 1, wherein the incident light is transmitted from the second collimator to the spectrometer by a fiber optic cable.

* * * * *